United States Patent [19]
Haynes et al.

[11] Patent Number: 5,972,366
[45] Date of Patent: Oct. 26, 1999

[54] DRUG RELEASING SURGICAL IMPLANT OR DRESSING MATERIAL

[75] Inventors: Duncan H. Haynes, Miami, Fla.; Ben H. Bodeker, Burtonsville; Mark D. Kline, Rockville, both of Md.

[73] Assignee: The Unites States of America as represented by the Secretary of the Army, Washington, D.C.

[21] Appl. No.: 08/710,439

[22] Filed: Sep. 17, 1996

Related U.S. Application Data

[62] Division of application No. 08/345,889, Nov. 28, 1994, Pat. No. 5,660,854.

[51] Int. Cl.$^6$ .............................. A61F 13/00; A61L 17/00; A61K 9/127
[52] U.S. Cl. ..................... 424/422; 424/423; 424/424; 424/425; 424/426; 424/427; 424/443; 424/444; 424/445; 424/450; 606/228; 606/230; 606/231
[58] Field of Search .................... 424/422–427, 424/450, 443–444; 606/228, 230, 231

[56] References Cited

U.S. PATENT DOCUMENTS

| | | |
|---|---|---|
| 2,430,740 | 11/1947 | Sharples . |
| 2,804,424 | 8/1957 | Stirn et al. . |
| 2,809,149 | 10/1957 | Cusumano . |
| 2,830,011 | 4/1958 | Parker et al. . |
| 3,987,797 | 10/1976 | Stephenson . |
| 4,024,871 | 5/1977 | Stephenson ..................... 128/335.5 |
| 4,027,676 | 6/1977 | Mattei ............................... 128/335.5 |
| 4,191,743 | 3/1980 | Klemm . |
| 4,373,519 | 2/1983 | Ervede ................................ 128/156 |
| 4,643,181 | 2/1987 | Brown ................................. 128/156 |
| 4,703,108 | 10/1987 | Silver et al. . |
| 4,837,285 | 6/1989 | Berg et al. . |
| 4,847,049 | 7/1989 | Yamamoto . |
| 5,006,071 | 4/1991 | Carter . |
| 5,061,689 | 10/1991 | Alvarez . |
| 5,116,620 | 5/1992 | Chvapil .................................. 424/445 |
| 5,133,965 | 7/1992 | Fountain . |
| 5,196,190 | 3/1993 | Nangia ................................. 424/78.06 |
| 5,197,977 | 3/1993 | Hoffman, Jr. et al. . |

OTHER PUBLICATIONS

Syrjanen, Stina M. et al., The Effects of Extraction Wound Healing . . . Complications, British Journal of Oral Surgery (1981); 57–66.

Boyes–Varley, J.G. et al., Effect of a Topical Drug Combination . . . Monkey, Int. J. Oral Maxillofac. Surg. (1988); 17:138–141.

Nadkarni, S.R. et al., Controlled Delivery of Pilocarpine . . . Matrices, Pharm. Res. (1993); 10(6):932 (abstract).

Nakamura, H. et al., Transcatheter Oily Chemoembolization . . . Carcinoma, Rad. Med. (1990); 8(5):188–90 (abstract).

*Primary Examiner*—Gollamudi S. Kishore
*Attorney, Agent, or Firm*—Blank Rome Comisky & McCauley LLP

[57] ABSTRACT

A surgical implant or external wound dressing which functions as both a hemostat and a device to safely and effectively deliver any of a number of pharmaceuticals to targeted tissue at a controlled rate is disclosed. The device generally comprises a carrier in the form of fibers, sutures, fabrics, cross-linked solid foams or bandages, a pharmaceutical in solid micoparticulate form releasably bound to the carrier fibers, and a lipid adjuvant which aids the binding of the microparticles to the fibers as well as their function in the body.

10 Claims, 3 Drawing Sheets

FIG. 1A
COLLAGEN MATRIX
10x

FIG. 1B
CELLULOSE MATRIX
10x

Visible Image DRY STATE

FIG.2A

Fluorescent Image DRY STATE

Visible Image HYDRATED STATE

FIG.2D

Fluorescent Image HYDRATED STATE

FIG. 3

DRUG RELEASING SURGICAL IMPLANT OR DRESSING MATERIAL

This is a divisional of co-pending application Ser. No. 08/345,889, filed Nov. 28, 1994 now U.S. Pat. No. 5,660,854.

FIELD OF THE INVENTION

The present invention relates to implantable absorbable sponges or externally applied dressing materials, and more particularly to implants or dressing materials having the capability to deliver pharmaceuticals or the like to the wound or implant site.

BACKGROUND OF THE INVENTION

In order to improve the effectiveness and functionality of wound dressings and surgical implants, various attempts have been made to incorporate them with a variety of medicaments such as antibiotics, analgesics, and the like.

Examples of antibacterial wound dressings are disclosed in U.S. Pat. No. 4,191,743 to Klemm et al., U.S. Pat. No. 2,804,424 to Stirn et al., and U.S. Pat. No. 2,809,149 to Cusumano. Similarly, U.S. Pat. No. 3,987,797 to Stephenson discloses a suture rendered antimicrobial.

Dressings which attempt to promote wound healing are disclosed in U.S. Pat. No. 5,124,155 to Reich. Most prior art surgical bandages and dressings which incorporate medications are made by soaking the material in an aqueous solution of the medicine. This can render the carrier brittle and inflexible upon drying. Moreover, it is difficult to control the rate of release of the medicament, or its effect on peripheral tissues, when it is applied to the carrier dissolved in a liquid state. Also, many important medicines are water insoluble and cannot be applied by this technique. Alternatively, the medicament is applied to the dressing or implant as a powder or dust which is quickly released and possesses a danger that large drug particles may irritate tissue or enter the circulatory system where they can block capillaries.

In addition to externally applied dressings, it is also known to impregnate an implantable surgical material with a medicament. For example, U.S. Pat. No. 5,197,977 to Hoffman Jr. et al. disclose a synthetic vascular graft that is impregnated with collagen and a medicament.

Additionally, Boyes-Varley et al. in *Int.J. and Maxillafac. Surg.* 1988; 17:138–141, describe the use in an animal study of a the Gelfoam® brand sponge with a saline solution of medicaments. However, the Physicians' Desk Reference, (Medical Economics, Co., Oradell, N.J.) 1992 edition warns that "it is not recommended that Gelfoam® be saturated with an antibiotic solution or dusted with antibiotic powder." A similar warning is provided with the entry of another popular surgical implant—the Surgicel® brand absorbable hemostat—which states that "the Surgicel® hemostat should not be impregnated with anti-infective agents."

It would be desirable to have a method for safely and effectively impregnating externally applied dressings as well as implantable sponges and hemostats, especially the popular Gelfoam® and Surgicel® brands. More particularly, it would be desirable to impregnate the dressings or implants with medicament in neither a solute nor a powder form, but a form which permits the drug concentration and release rate to be controlled.

SUMMARY AND OBJECTS OF THE INVENTION

In view of the foregoing limitations and shortcomings of the prior art methods, materials, and compositions, as well as other disadvantages not specifically mentioned above, it should be apparent that there exists a need in the art for a surgical implant and external wound dressing which can safely and effectively deliver any of a number of pharmaceuticals (or drugs) to targeted tissue at a controlled rate, while maintaining its hemostatic function. It is, therefore, a primary object of this invention to fulfill that need by providing a surgical implant, sponge, or wound dressing with such drug delivery and hemostatic capability.

More particularly, it is an object of this invention to provide an absorbable carrier which is adapted to take up and controllably release a drug in solid, microparticulate form with the advantage that the drug concentration and release can be controlled.

It is another object of the invention to provide a device of the aforesaid type wherein the drug is water insoluble.

It is another object of the invention to provide a device of the aforesaid type wherein the drug can be prevented from entering tissues or circulatory system, if desired.

It is another object of the invention to provide a device of the aforesaid type wherein the drug particles have a diameter of less than 10 microns so as to diminish the likelihood that the particles will irritate tissue if released or block capillaries if the particles enter the circulation It is another object of the invention to provide a device of the aforesaid type wherein the drug in microparticulate or microcrystalline form is protected against oxidation and possible reaction with the dressing material.

It is another object of the invention to provide a device of the aforesaid type wherein the carrier is adapted to retain as much as 4 grams of drug per gram of carrier.

It is another object of the invention to provide a device of the aforesaid type wherein the carrier remains flexible rather than brittle.

It is another object of the invention to provide a controlled release drug delivery system for dispensing antiseptics, antibiotics, anti-inflammatories, local anesthetics, tissue growth promoters, or tissue destruction inhibitors to a wound or surgical site, including both soft tissue and bone, for the purpose of providing hemostasis, relief of pain, control of infection, hastened regrowth, decreased inflammation, prevention of keloid formation and hastened recovery.

Briefly described, the aforementioned objects are accomplished according to the invention by providing a wound dressing, sponge, or surgical implant material comprising a carrier material, a pharmaceutical composition in solid microparticlulate or microcrystalline form, and an adjuvant coating to improve the adherence of the pharmaceutical particles to the carrier and to control the rate of release and the concentration of the pharmaceutical to the wound site.

The carrier material of the present invention may be made of any of a variety of materials which are pharmaceutically acceptable (non-toxic and non-allergenic), adhere to or within the target tissue, and incorporate the pharmaceutical composition. Preferably the carrier is fibrous, such as a fabric dressing and suture or a cross-linked solid foam adsorbable implant, wherein the fibers support the drug particles.

The types of pharmaceuticals which may be employed include antiseptics, antibiotics, anti-inflammatories, local anesthetics, analgesics, tissue growth promoters, and tissue destruction inhibitors, for example. The pharmaceutical composition is preferably a crystalline or microparticulate, water-insoluble drug reduced to microscopic dimensions (20 nm–30μ) by sonication, microfluidization (Example 1) and other methods of high-shear homogenization such as the Gaulin or Rannie Homogenizers (APV Gaulin/Rannie, St. Paul, Minn.), or other processes. The microcrystals are suspended in an aqueous solution by coating the crystals with an amphipathic, membrane-forming lipid. This lipid also acts as an adjuvant allowing the drug microparticles to attach to the carrier material by non-covalent means. The saturated carrier material preferably comprises microscopically-dimensioned empty space, allowing for hydration, efflux of drug and ingrowth of tissue. Also storage of the drug in microparticulate or microcrystalline form protects it against oxidation and possible reaction with the dressing material.

The invention provides a pliable, implantable, as well as externally-applicable surgical material which contains a drug, at high concentration. Upon application to a surgical site or wound, the material releases the drug to the surrounding tissue at rates and durations chosen for optimal therapeutic effect. Some embodiments of the invention produce a semi-solid material suitable for implantation in bone.

The method of making the present invention generally comprises the steps of selecting a carrier material, such as an implantable absorbable sponge or hemostat, preparing a drug to microparticulate form, coating the particles in an adjuvant, modifying the carrier to improve its cohesive characteristics, and applying the coated drug particles to the carrier, and removing the water by lyophilization.

The implant of the present invention may be used in surgical or dental procedures wherein it is desired to simultaneously control bleeding and deliver a drug to adjacent tissue in a sustained manner. In particular, contemplated uses include implantation of compositions containing drugs and appropriate factors to provide pain relief, to control inflammation, to accelerate tissue or bone regrowth and to control infection.

The present invention provides a means of giving continuous treatment of a wound or surgical site with a drug. When used with a resorbable carrier material, our invention provides an implantable sustained delivery device for the drug, achieving local therapeutic benefit while providing hemostasis and a controlled environment for tissue regeneration. It provides a large reservoir of drug at the site where it is needed, but in the form of drug microparticle with controlled association with the carrier matrix material. The present invention is distinctly advantageous over extemporaneous preparations in which macro-particulate drug is "dusted" into wound dressings or surgical materials. Accompanying such practice is the danger that large drug particles may be released to irritate tissue or to enter the circulation where they can block capillaries.

BRIEF DESCRIPTION OF THE DRAWINGS

FIGS. 1–D are schematized drawings made from microscopic observations of Lecithin-Oxytetracycline-Collagen Matrix and Lecithin-Oxytetracycline-Cellulose Matrix at 10× and 40×.

DETAILED DESCRIPTION OF THE INVENTION

The present invention generally comprises a fibrous carrier matrix, which functions as a wound dressing, sponge, absorbable surgical implant or the like, a pharmaceutical composition in solid microparticlulate or microcrystalline form, and an adjuvant coating to improve the adherence of the pharmaceutical particles to the carrier and to improve control over the concentration and rate release action of the pharmaceutical.

STARTING MATERIALS

Carrier Matrix

The carrier of the present invention may be made of any of a variety of materials which are pharmaceutically acceptable (non-toxic and non-allergenic), which can adhere to or be implanted within the target tissue, and which can be made to incorporate the pharmaceutical composition. The carrier is preferably fibrous, such as textiles, filaments, cross-linked solid foam, gels, etc. Exemplary materials include, but is not limited to, collagen, chemically cross-linked collagen or gelatin, cellulose, oxidized cellulose; cellulose acetate in fibrous form, especially those with a low degree of acetylation; ethyl cellulose, methyl cellulose, cellulose ethyl hydroxyethyl ether in fibrous form; poly-D,L-lactate; pyrrolidone polymers in fibrous form; acrylic resins, including polyacrylate, polymethacrylate, and their copolymers, polyhydroxybutyrate, poly-hydroxyvalerate and their copolymers, in fibrous form; polyglycolic acid (Dexon), poly(D,L-lactic-co-glycolic acid); and polyglactin (Vicryl). The preferred carrier material contains microscopically-dimensioned empty space, allowing for hydration, efflux of drug and ingrowth of tissue.

As used herein, the term "matrix" or "matrix material" describes the carrier material in a three dimensional configuration (fabrics, piled fibers, solid foams, etc.). The matrix of the present invention functions not only as a carrier for the pharmaceutical but also as a wound dressing, implantable hemostat, or the like. Accordingly, it is preferable to utilize as the carrier matrix a wound dressing or implantable hemostat which is commercially available and determined to be safe and effectively loaded with antibiotics and other pharmaceuticals.

An example of a surgically implantable material which may be employed is the Gelfoam® brand absorbable gelatin sterile sponge (Upjohn Company, Kalamazoo, Mich.) which is widely used in surgery and dentistry. This product is described in the Physicians Desk Reference, 1992 ed. at page 2338 as a "water-insoluble, off-white, nonelastic, porous pliable product prepared from purified pork skin gelatin USP granules". It functions as a hemostat which is able to absorb and hold within its interstices, many times its weight of blood and other fluids. The directions for use state that Gelfoam® may be left in place and the wound may be closed over it. Under "Precautions", it is stated that "It is not recommended that Gelfoam® be saturated with an antibiotic solution or dusted with antibiotic powder." It is a particular feature of the present invention that this and similar materials are modified to be safely and effectively loaded with antibiotics and other pharmaceuticals.

Another example of a surgically implantable material which may be employed is the Surgicel® Absorbable Hemostat (Johnson & Johnson Medical, Inc., Arlington Tex.). This product comprises knitted fabric strips of oxidized regenerated cellulose, sterile-packaged in various sizes described in the Physician's Desk Reference, 1992 ed. at page 1151 as having both hemostatic and bactericidal properties. Instructions are given for use as both a removable dressing and as an implantable material when applied in small quantities. Under "Warnings", it is stated that "Surgicel® hemostat should not be impregnated with anti-infective agents or with other materials such as buffering or hemostatic substances." However, the method of the present invention modifies this and related products made of cellulose fibers so as to deliver drugs.

Other fiber-based surgical materials to which the present invention is applicable, including calcium-alginate in fibrous form (Lubet-Moncla, U.S. Pat. No. 3,431,907, 1969), materials incorporating cross-linked gelatin, carboxy-methyl cellulose or pectin, Pawelchak et al., U.S. Pat. No. 4,292,972, 1981, and prior art discussion therein, and flocculated or chemically cross-linked fibronectin (Reich, U.S. Pat. No. 5,124,155, 1992). This listing is for illustrative purposes, and is not considered limiting.

The carrier may be sized and shaped in any manner suitable to conform to the particular body cavity or tissue to which it will be applied. The bulk density of the carrier matrix should be sufficiently low to allow adequate amounts of the pharmaceutical to be incorporated, while maintaining the structural integrity. For implantation, the carrier matrix should be biodegradable and non-allergenic. The microscopic size of the carrier material is limited only by the size of the cavity to be packed and the burden of material to be resorbed. The lower limit of size is likewise determined by considerations of retention in the cavity. The size and density of individual fibers in a fabric or solid foam is limited by considerations of mechanical strength and porosity. Generally, the larger the microscopic size and the lower the porosity, the slower will be the drug release.

Pharmaceuticals

The pharmaceutical component (or drug) of the present invention may be any of a variety of substances including antiseptics, antibiotics, anti-inflammatories, local anesthetics, tissue growth promoters, and tissue destruction inhibitors which are solid in the pure state at and below 37° C. Most preferably, the drug substance is reduced to $\leq 10\,\mu m$ or submicron dimensions in an aqueous medium by sonication process, microfluidization, or homogenization described in U.S. Pat. Nos. 5,091,187 and 5,091,188 to Haynes, both incorporated herein by reference. In the Haynes process, water-insoluble drugs are rendered injectable by formulation as aqueous suspensions of phospholipid-coated microcrystals. The crystalline drug is reduced to 50 nm to 10 um dimensions by sonication or other processes inducing high shear in the presence of phospholipid or other membrane-forming amphipathic lipid. The membrane-forming lipid stabilizes the microcrystal by both hydrophobic and hydrophilic interactions, coating and enveloping it and thus protecting it from coalescence, and rendering the drug substance in solid form less irritating to tissue.

The pharmaceutical composition is preferably a crystalline or microparticulate, water-insoluble drug reduced to microscopic dimensions (20 nm–30 $\mu$m) by sonication, microfluidization, homogenization, wet grinding or air impact, or other processes. The microcrystals, which may be water insoluble, are suspended in an aqueous solution by coating the crystals with an amphipathic, membrane-forming lipid. The drug microparticles are attached to the carrier material by non-covalent means, using an adjuvant material. The loaded carrier material preferably comprises microscopically-dimensioned empty space, allowing for hydration, efflux of drug and ingrowth of tissue.

In preferred embodiments of the invention, the selected drug will be substantially water-insoluble ($\leq 20$ mg/ml at physiological pH). Thus, diffusible drug monomers will be present at only low concentration when the carrier matrix is hydrated. Water-insolubility is also associated with slow dissolution rates. The resulting slow release is desirable for most therapeutic use.

In cases where incorporation and slow release of a water-soluble drug is required, the drug may be rendered water-insoluble by complexation with an oppositely-charged cation or anion as described in the next paragraph. Alternatively, the release of water-soluble drugs can be slowed by coating their drug microparticles with lecithin or other membrane-forming lipids.

As described by Haynes (U.S. Pat. Nos. 5,091,187; 5,091,188) many water-soluble drugs can be held in drug microcrystal form by complexation with anions and cations. These include 2-naphthylenesulfonate (napsylate), gluconate, 1,1' methylene bis (2-hydroxy-3-naphthalene) carboxylic acid (pamoate), tolylsulfonate (tosylate), methanesulfonate (mersylate), glucoheptanoate (gluceptate), bitartrate, polyglutamic acid, succinate, carboxylic acids of various chain lengths from acetate to behenate, bromide, iodide, phosphate, nitrate, calcium, magnesium, their 1:1 fatty acid or phosphate complexes, and with various amines, including dibenzylethylenediamine (benzathine), N,N' (dihydroabietyl)ethylene diamine (hydrabamine) or polymers such as polylysine. The choice of these counterions is made largely on an empirical basis, with stability of the derived crystals and their compatibility with water being primary criteria. As described by Haynes (U.S. Pat. No. 5,246,707) these principles can also be used to render biological molecules insoluble. It is also applicable to water-soluble drugs, particularly those which can be rendered water-insoluble or which do not cross lipid bilayer membranes.

As previously stated in U.S. Pat. Nos. 5,091,187, 5,091,188 and 5,246,707 to Haynes, the size of the drug microparticles can vary within large limits which are set by the desired rates of release of the drug and by physical stability and mechanical properties of the final product. The size of the drug microparticles can be chosen to optimize the rate of release of the drug. Generally smaller particles give faster release. The dimensions of the drug microparticles can vary between 30 $\mu$m and 20 nm. Preferred is when the upper limit of drug microparticle size is 10 $\mu$m so that capillary blockage will not occur in the event that drug microparticles are released to the circulation. A most preferred range is between 2 $\mu$m and 100 nm, which is largely determined by the size relationship between the drug microparticle and the fibers of the carrier material and the desire for pliability of the final product. Generally, the smaller the drug particles, the smaller will be the rate of release. In actual practice, optimal particle size is determined empirically by testing a range of sizes and noting physical and release characteristics of the product.

If the incorporated drug is not bacteriostatic or bactericidal, additional agents may be incorporated. A wide range of preservatives can be incorporated. These include, but are not limited to, benzalkonium chloride, benzethonium chloride, propylparaben, butylparaben, chlorobutanol, benzyl alcohol, phenol, sodium benzoate, EDTA, etc. The product may be terminally sterilized by gamma irradiation or, in some cases, by ethylene oxide or heat.

Adjuvant

A particular feature of the present invention is its use of adjuvant materials to control the mode of association between the drug microparticles and the carrier material. The adjuvant aids the incorporation of the drug microparticles in the carrier material by at least one of two mechanisms: (a) by simultaneously coating the drug microparticles and the fibers of the carrier material to promote their association, and/or (b) by aiding in the entrapment of drug microparticles between fibers of the carrier material while the two are being subjected to physical or physico-chemical manipulations (not forming covalent chemical bonds). It is possible for an adjuvant to work by both mechanisms. Membrane forming phospholipids such as lecithin can simultaneously envelope the drug microparticles and fibers of the carrier material. Fiber-forming materials such as solubilized collagen will coat both the drug microparticles and fibers of carrier material.

The mode of association between the drug microparticle and the carrier material can be:

(a) by binding of the drug microparticle to the carrier material by means of the adjuvant which has chemical affinity for both, (b) by entrapment of the drug microparticle between fibers of the carrier material, facilitated by physical or non-covalent chemical manipulations of the carrier material together with the drug microparticle in the presence or absence of adjuvant, (c) by the naturally occurring chemical affinity which may occur between the surfaces of the drug microparticles and the fibers of the carrier material in selected cases. This can be determined by adding drug microparticles to single fibers of the carrier material and observing their interactions under a microscope. These forces can include hydrophobic interaction, hydrogen bonding and ionic interactions. When strong binding forces are present, and an adjuvant will not be needed.

Membrane-forming adjuvants which may be used include the phospholipids, including lecithin (phosphatidyl choline), phosphatidyl glycerol, phosphatidic acid, phosphatidyl serine, phosphatidyl inositol, cardiolipin (diphosphatidyl glycerol), phosphatidyl ethanolamine; sphingomyelin; and mono-glycerides, including monopalmitin, monostearin, monocaprylin and monoolein. As described in U.S. Pat. No. 5,091,188, other lipid materials can be included with them to modify the properties of the resulting membranes. Also, water-soluble and water-suspendable adjuvants include collagen (several types); gelatin; carboxymethylcellulose, hydroxyethyl cellulose, hydroxypropyl cellulose, hydroxypropyl methylcellulose, povidone, benzalkonium chloride and benzethonium chloride. Non-ionic surfactants can also be used as adjuvants to aid drug microparticle loading and release, and for their anti-bacterial properties. These include polyoxamers such as polyoxyl 10 oleyl ether, polyoxyl 20 cetostearyl ether, polyoxyl 35 castor oil; polyoxyl stearates, polysorbates; polypropyleneglycol; sorbitan monolaurate, sorbitan monooleate, sorbitan monopalmitate and -monostearate. Miscellaneous adjuvants include cholesterol, calcium stearate, magnesium stearate; sodium salts of fatty acids such as sodium stearate; sodium lauryl sulfate; and glycerol monstearate, Selection of Secondary Adjuvant:

Water-soluble macromolecules capable of binding drug monomers can be incorporated in the preparation to increase the total concentration of the drug in the aqueous microphase and speed the release of the drug. These include serum albumin and cyclodextrans (alpha, beta and gamma). Alternatively, carboxymethylcellulose, dextrans and other water-soluble polymers can be added to the preparation to increase the viscosity of the aqueous phase, and thus slow the rate of diffusion of drug monomers and drug microparticles in the aqueous microphase.

It is believed that the present invention is superior to prior art modes of association of particulate drug which neither involve adjuvants nor rely on specific interaction between the drug particle and the fibers of the carrier material. such as simple retention of drug particles in the interstices of an unperturbed solid foam or fabric of the carrier material by simple "dusting in" or by air flow (as in entrapment of dust particles in air filters). Materials which can be "blown in" can also be shaken out during transport and handling. Furthermore, our invention does not rely on binding of monomeric drug molecules to the carrier material or the adjuvant, although such tendencies may slow or speed the release of the drug (respectively).

Thus, a particular feature of the present invention is that it relies on a specific physical association between drug microparticle and the solid carrier matrix. We achieve this by use of the adjuvant or by specific manipulations of the carrier material in the presence of the drug microparticles. This provides a surgical material in which the drug microparticles remain homogeneously distributed in storage, during transport and when the material is cut and worked.

METHODS OF MANUFACTURE AND USE

Manufacture of the present invention begins with selecting a fibrous carrier material, such as an implantable absorbable sponge or hemostat, selecting a drug and selecting the adjuvant (membrane forming, water soluble, etc.).

There are two preferred methods of introducing the drug and adjuvant into the carrier material: (a) by soaking the carrier material with a suspension of water insoluble drug microparticles in the presence of the adjuvant, or (b) by soaking the carrier material in a solution of the drug in the presence of adjuvant, followed by removal of solvent, thereby producing microparticles. Method (a) is particularly applicable where the drug is poorly soluble in the chosen solvent and where a high degrees of drug loading and pliability of the finished product are desired.

In Method (a), when the solvent is water, the preferred method of removal of the solvent is freeze-drying (lyophilization), particularly for an aqueous solvent (Examples 2–3). Removal of water in the frozen state avoids rearrangement of the drug microparticles and deposition of solubilized drug as a continuous phase between the microparticles, which results in hardening of the dressing or implant.

Method (b) is applicable when lower degrees of loading are required and when ease of production is important. In this case freeze-drying is not generally advantageous over simple solvent evaporation. It is possible to do the coating by several stages of soaking and evaporation (Example 8).

The choice between these two methods can be based on systematic investigation with the desired drug and adjuvant combination. Our experimentation has given indications that addition of drug microparticles to hydrated carrier material enhances their subsequent entrapment between the fibers. Also, the interaction of the drug microparticle with the fibers of the carrier material is strengthened by the subsequent dehydration, particularly in the presence of a suitable adjuvant. Adjuvants which have affinity for both the drug microparticle and the carrier material are most suitable for producing tight association of the latter two.

When pliable materials are desired, it is important that the drug microparticles or dissolved drug not form a continuous drug phase within the preparation. This can occur when the solvent removal is from a liquid state and when the carrier material acts as a wick.

It is also possible to introduce the drug to the carrier material by spraying on a solution or suspension of drug, in the presence or absence of adjuvant. This method is particularly applicable when high degrees of drug loading are not necessary and when ease of manufacture is important.

Rate of release of the Drug:

Mechanisms by which the drug can be released from the carrier include: (a) diffusion or flow of drug monomers and (b) diffusion or flow of drug microparticles from the carrier matrix. Mechanism (a) is most important when the drug microparticles are firmly attached to the carrier material or are entrapped therein. It is illustrated by examples 5, 11 and 17 in which oxytetracycline (OTC), a water-insoluble drug, was released very slowly. The higher the number of grams of water-insoluble drug per liter volume of matrix, the slower will be its release rate in terms of fraction per hour.

Rates of release by mechanism (a) will be lowest for drugs which are intrinsically water insoluble. However, low rates of release of water-soluble drugs can also be achieved if they are rendered water-insoluble by complexation with suitable cationic or anionic agents or by secondary adjuvants (described above) to make drug microcrystals. Also, the rates of release of water-soluble drugs can be decreased if they are intrinsically membrane impermeable and are encapsulated within membrane vesicles of lecithin or other membrane-forming lipids firmly attached to the carrier material.

The rate of release of a water-insoluble drug via mechanism (a) can be increased by inclusion of water-soluble macromolecules such as serum albumin or cyclodextrin which have appreciable ability to bind the drug monomers (secondary adjuvants). After the matrix is implanted within the body and becomes hydrated, these molecules will bind drug monomers, thus increasing their total concentration in the aqueous diffusion pathways within quiescent matrix. This will allow for more rapid delivery of the drug from the matrix interior to the tissue boundary.

When mechanism (b) is operative, the rate of loss of the drug is dependent upon the rate of release of the drug microparticles from the carrier material. In examples 13, 14, 15 and 16, oxytetracycline microparticles were released by this mechanism. The rate of release of drug microparticles is dependent upon the firmness of attachment to (or entrapment within) the carrier material, which can be controlled by selection of primary adjuvant materials. Since diffusion of large particles is slow, the rate of release is dependent on the amount of tidal flow resulting from squeezing and releasing of the preparation in the medium in which it is placed. Thus the inclusion of secondary adjuvants which increase the viscosity of the aqueous microphases within the hydrated matrix can be used to decrease the rate of release by mechanism (b).

The design of a particular product will start by deciding on the amount of drug to be loaded and on the rate at which it is to be released. Then the physico-chemical and solubility characteristics of the drug compound will be considered. Then a combination of carrier material and adjuvants will be chosen to favor or disfavor mechanisms (a) and (b) to obtain the desired release rate. For example, if the drug is intrinsically water-insoluble and slow rates of release are desired, then a carrier material/adjuvant combination favoring entrapment and release by mechanism (a) will be selected (examples 5, 11 and 17). But in the case where it was desired to release the same drug more rapidly, a carrier material/adjuvant combination favoring attachment by coating and release by mechanism (b) will be selected (examples 13, 14, 15 and 16).

If a water-soluble drug is used, the principles are different. In this case adjuvants are chosen which will encapsulate the drug and/or render it insoluble. As an example, hydrophilic, water-soluble drugs which bear net charge at neutral pH can be entrapped within vesicular structures produced by membrane-forming phospholipids. Also, many water-soluble drugs bearing net charge can be rendered insoluble by a counterion of opposite charge. Both of these principles can be combined to hold a water-insolubilized drug inside lecithin vesicular structures attached to or entrapped within the carrier material.

Design of final product:

The design of the final product will depend upon how the product is to be used (dressing vs implant), the desired size and shape of the material, and the desired release rate and duration of release. The functioning of the product depends on six variables listed below, with brief illustrations following in parentheses:

a. Carrier material (biodegradable for implantation; pliable for application to soft tissue, stiff for implantation in bone; porosity).

b. Size of drug microparticle or microcrystal (less than 10 $\mu$m for implantation; dimensions less than diameter of fibers for optimal coating; dimensions comparable with interstices of carrier material for optimal entrapment; small dimensions for more rapid dissolution).

c. Adjuvant (to coat or aid in entrapment of the drug microparticle; choice of mechanism (a) or mechanism (b) for release of drug).

d. Method of solvent removal (lyophilization or simple evaporation determined by economics and stiffness and homogeneity requirements of finished product).

e. Degree of drug loading, density of preparation (gm drug/ml hydrated matrix and gm drug/gm carrier material+adjuvant; determined by potency of the drug and desired number of hours of sustained release).

f. Secondary adjuvants (to increase or decrease the solubility of the drug or alter the viscosity of the bulk material in the hydrated state, thus altering rate of drug release).

In describing the various embodiments of our invention, we will use the following notation:

(Adjuvant)-(Drug)-(Matrix Material).

Thus the composition of Example 2 is Lecithin-Flurbiprofen-Collagen Matrix.

The following examples are given to show the manner by which our invention is carried out. All parts and percentages reported herein are by weight (w/w) or weight/volume (w/v) percentage, in which the weight or volume in the denominator represents the total weight or volume of the system. We also report drug loading in terms of gm drug per gm of matrix material. Concentrations of water soluble constituents in aqueous solution (e.g. glucose) are given in millimolar concentration (mM=millimoles per liter) referred to the volume of water in the system. All temperatures are reported in degrees Celsius. Diameters or dimensions are given in millimeters (mm=$10^{-3}$ meters), micrometers ($\mu$=$10^{-6}$ meters) or nanometers (nm=$10^{-9}$ meters). The compositions of the invention can comprise, consist essentially of or consist of the materials set forth and the process or method can comprise, consist essentially of or consist of the steps set forth with such materials.

EXAMPLE 1

Gelfoam® Impregnated with Aqueous Suspension of Lecithin-Coated Flurbiprofen Microcrystals This example describes soaking Gelfoam® with an aqueous suspension of microcrystals to obtain a product lacking sustained release or specific association of the drug with the carrier material. Lecithin-coated microcrystals of flurbiprofen were prepared by the method described in U.S. Pat. Nos. 5,091,187 and 5,091,188 to Haynes which are incorporated herein by reference. Briefly, 75 gm egg lecithin (Pfanstiehl Laboratories, Waukegan, Ill.), Phospholipids, egg, #P-123, Lot 21097, Drug Masterfiled) was added to 225 ml with 300 mM glucose, 2 mM sodium phosphate buffer, pH 7.0. The mixture was allowed to hydrate and was then dispersed with a Brinkman Polytron PR 10/35 apparatus (Brinkman Instruments, Westbury, N.Y.). Then 75 gm of flurbiprofen (SST Corp, Clifton, N.J.) were added and further dispersed. The suspension was then degassed by sonication and was passed a total of 7 times through an M-110F Microfluidizer (Microfluidics, Inc., Newton, Mass.) to create an aqueous suspension of lecithin-coated microcrystals of flurbiprofen (20% (w/v) flurbiprofen, 20% (w/v) lecithin). The pH was adjusted to 7.2.

The preparation was examined under a fluorescence microscope (Carl Zeiss, #4725631, "West Germany") at 800-fold magnification in fluorescent and in normal mode. Small free-flowing microcrystals of approx. 0.5 $\mu$m dimension were visualized by their refraction and by their greenish fluorescence. We estimate that less than 1% of the particles were greater than 1.0 $\mu$m dimension, and essentially none were greater than 10 $\mu$m. Analysis with a Coulter N4 Particle Sizer (Coulter Electronics, Hialeah, Fla.) in the "intensity" mode gave an average diameter of 521±62 nm for 100% of the particles, and 0%>3 $\mu$m.

Samples of Gelfoam® (NDC 0009-0342-01, Gelfoam, Sterile Sponge, absorbable gelatin sponge, USP (Upjohn Company, Kalamazoo, Mich.) were cut into 7 mm×7 mm×10 mm pieces. The volume of the cut samples was estimated as approx. 0.5 cm$^3$ from their dimensions. The samples were weighed and then immersed in aliquots of the 20% (w/v) flurbiprofen, 20% (w/v) lecithin-coated microcrystal suspension described above and were subjected to three squeezing/reexpansion cycles. The samples were then removed by means of a surgical forceps and allowed to drip. The hanging samples retained approx. 0.1 ml (cm$^3$) of the microcrystal suspension as determined weighing. The volume of the sample was estimated to be less than 0.25 ml. Some of the samples were introduced into vials containing mannitol solution and were observed to return to their original volumes of 0.5 cm$^3$. Additionally, the flurbiprofen microcrystals could be readily removed by squeezing, indicating a lack of specific association with the collagen carrier material.

The resulting product constitutes a hemostatic plug which can be introduced into tooth sockets after tooth extraction for the purpose of controlling bleeding and delivering the non-steroidal anti-inflammatory analgesic drug to the tissue for the control of pain. The material can be removed days after surgery or a gum flap can be sewn over, enclosing the material which will eventually be resorbed. This material can also be used for many other types of surgery where fairly rapid release of the drug is desired.

EXAMPLE 2

Lecithin-Flurbiprofen-Collagen Matrix

This example shows how freezing and lyophilization of the product of Example 1 results in specific association between the flurbiprofen microcrystals and the collagen fibers as described for our invention. The impregnated material of Example 1 was placed in glass ampules, sealed, and was quickly frozen by partial immersion of the ampules in $CO_2$-acetone. Then the ampules were uncapped and introduced into a lyophilizer. After reaching dryness, the ampules were removed, capped and terminally sterilized by gamma irradiation (1.5 mega Rad).

Some of the ampules were opened and the contents were analyzed. The sponges maintained their shape but were reduced in volume to less than 0.2 cm$^3$. They were slightly more rigid than before impregnation and lyophilization. They were slightly tacky. When gently compressed and released they returned to their original shape. When compressed under high pressure they did not return to their original dimensions. Compression did not cause the drug to be lost from the matrix. Some samples were cut with crossed scalpels and were examined under the fluorescent microscope at 800-fold magnification in fluorescent and normal modes. Collagen fibers were discernible by a very weak greenish fluorescence in the dry state. These were coated with approx. 0.5 $\mu$m crystals of oxytetracycline OTC (strong yellow-green fluorescence) closely associated with the fibers. Occasionally the crystals occurred in clusters, also closely associated with the fibers.

Buffer (300 mM mannitol, 2 mM sodium phosphate, pH 7.0) was added to the microscope slides and the process of rehydration was observed. The drug microcrystals remained associated with the fibers. In the first phases of the rehydration process, lamellar structures coating the fibers in association with the microcrystalline drug became prominent. These lamellar structures are similar to what is observed when solid lecithin is hydrated under similar conditions. Upon agitation of the hydrated samples by manipulation of the cover slip, some clusters of microcrystals could be made to detach from the carrier material.

One 10 mm×7 mm×7 mm Lecithin-Flurbiprofen-Collagen matrix composition was introduced into an ampule containing an excess of mannitol buffer. The matrix returned to its original 0.5 cm$^3$ volume within a few minutes. In contrast to Example 1, squeezing does not release flurbiprofen microcrystals. After 2 hrs of rehydration, it was removed and blotted onto a microscope slide. Distinct 0.5 $\mu$m to 4 $\mu$m lecithin-coated flurbiprofen microcrystals were observed. The blot contained a small amount of collagen which could be detected by its weak green fluorescence. The sponge was torn apart and a fragment was viewed on a slide. It contained 0.5 $\mu$m to 4 $\mu$m lecithin-coated microcrystals of flurbiprofen, identified by its strong green fluorescence, within a continuous collagen matrix. The properties of the lecithin-flurbiprofen-collagen matrix in the dry state are shown below in TABLE 1.

TABLE 1

| | |
|---|---|
| Approx. volume | 0.5 ml |
| Gelfoam ® weight | 5.9 ± 0.4 mg |
| Flurbiprofen weight | 25.6 ± 4.3 mg |
| Physical state | Pliable, solid foam |
| Color | Yellow/light brown |
| Flurbiprofen MC dist. (Macroscopic) | Homogeneous |
| Flurbiprofen MC assn. | Very Close |
| Rehydration time | Approx. 1 min |
| Physical characteristics after rehydration | Sponge |
| Drug behavior after rehydration | Remains in sponge |

The resulting product constitutes a sterile hemostatic plug which can be conveniently introduced into tooth sockets after tooth extraction for the purpose of controlling bleeding and and for delivering the non-steroidal anti-inflammatory analgesic drug to the tissue for the control of pain. The lecithin. More information on the method of preparation is given in the corresponding examples. Each row of Table 2 describes the properties of a separate product.

TABLE 2

| Preparation | Carrier wt. (mg) | OTC wt. (mg) | Phys. State | OTC Dist. (macro.) | Assoc. | Release Rate |
|---|---|---|---|---|---|---|
| 20% Lecithin - 20% OTC - Collagen Matrix | | | | | | |
| Heat | 8.2 ± 0.7 | 26.6 ± 6.1 | Shr./hrd. | Homog. | SCB | Slow |
| Vacuum | 7.8 ± 0.6 | 15.4 ± 2.6 | Hrd. | Homog. | CA | Slow |
| Lyophilized | 6.8 ± 0.7 | 21.4 ± 2.4 | Pliable | Homog. | CA | Slow |
| 20% Lecithin - 20% OTC - Cellulose Matrix | | | | | | |
| Heat | 26.8 ± 0.4 | 64.3 ± 0.1 | Pliable; dark. | Homog. | CCA | Slow |
| Lyophilized | 31.2 ± 5.0 | 71.5 ± 1.4 | Pliable | Homog. | CCA | Slow |
| 20% OTC - Collagen Matrix | | | | | | |
| Lyophilized | 16.0 ± 0.7 | 5.2 ± 3.4 | Pliable | Heterog. | LA | Rapid |
| 20% OTC - Cellulose Matrix | | | | | | |
| Heat | 27.1 ± 0.4 | 58.5 ± 11.2 | Pliable | Heterog. | VLA | Rapid |
| Lyophilized | 31.8 ± 1.1 | 73.7 ± 1.6 | Pliable | Heterog. | VLA | Rapid |
| 2% Collagen - 20% OTC - Collagen Matrix | | | | | | |
| Heat | 6.3 ± 0.1 | 17.4 ± 2.5 | Shr./hrd. | Homog. | SCB | Very slow |
| Lyophilized | 6.1 ± 0.2 | 14.9 ± 1.8 | Crusty/hrd. | Homog. | SCB | Very slow |
| 2% Collagen - 20% OTC - Cellulose Matrix | | | | | | |
| Heat | 30.7 ± 1.1 | 63.2 ± 1.2 | Crusty/hrd. | Homog. | LA, flakes off | Rapid |
| Lyophilized | 34.2 ± 0.6 | 67.8 ± 6.7 | Crusty/hrd. | Homog. | LA, flakes off | Rapid |
| 1% PEG - 20% OTC - Collagen Matrix | | | | | | |
| Heat | 7.3 ± 1.4 | 22.4 ± 1.8 | Shr./hrd. | Homog. | VLA | Rapid |
| Lyophilized | 6.9 ± 0.3 | 21.5 ± 2.5 | Crusty/stiff | Homog. | VLA | Rapid |
| 1% PEG - 20% OTC - Cellulose Matrix | | | | | | |
| Heat | 37.9 ± 1.7 | 90.8 ± 24.6 | Pliable | Heterog. | VLA | Rapid |
| Lyophilized | 44.7 ± 1.8 | 123.1 ± 1.0 | Pliable | Homog. | VLA | Rapid |
| 1% CMC - 20% OTC - Collagen Matrix | | | | | | |
| Heat | 6.7 ± 0.2 | 20.7 ± 2.3 | Shr./hrd. | Homog. | LA | Slow |
| Lyophilized | 6.9 ± 0.2 | 22.5 ± 8.1 | Crusty/hrd. | Homog. | VLA | Rapid |
| 1% CMC - 20% OTC - Cellulose Matrix | | | | | | |
| Heat | 43.4 ± 0.6 | 111 ± 15 | Crusty/hrd. | Homog. | VLA | Rapid |
| Lyophilized | 42.7 ± 1.3 | 98.5 ± 5.1 | Crusty/hrd. | Heterog. | VLA | Rapid |
| 2% Lecithin - 2% OTC - Collagen Matrix (prepared from EtOH soln.) | | | | | | |
| Vacuum | 7.1 ± 0.6 | 10.7 ± 1.7 | Pliable | Homog. | VCA | Slow |
| 2% Lecithin - 2% OTC - Cellulose Matrix (prepared from EtOH soln.) | | | | | | |
| Vacuum | 41.1 ± 1.6 | 19.2 ± 2.6 | Pliable | Homog. | CA | 1/2 Rapid 1/2 Slow |
| 2% OTC - Collagen Matrix (prepared from EtOH soln.) | | | | | | |
| Vacuum | 7.9 ± 0.6 | 16.3 ± 1.3 | Pliable | Homog. | 1/2 CA 1/2 VLA | Slow Rapid |
| 2% OTC - Cellulose Matrix (prepared from EtOH soln.) | | | | | | |
| Vacuum | 38.8 ± 4.7 | 12.8 ± 2.8 | Pliable | Homog. | VLA | Rapid | material can be removed days after surgery. Alternatively, a gum flap can be sewn over, enclosing the material which will eventually be resorbed. This material can be used for many other types of surgery in which fairly rapid release of the drug in microparticulate form (cf. FIG. 3) is desired.

EXAMPLES 3–9

Table 2 presents the results for preparations of surgical materials incorporating the antibiotic oxytetracycline (OTC) using Gelfoam® or cellulose gauze (Johnson & Johnson, New Brunswick, N.J.) as the matrix material. In addition to being a useful antibiotic, OTC has an intrinsic fluorescence which aids in visualizing its deposition in the the dressing. The left-hand column describes the method of manufacture of the product. OTC microcrystals (20%) were coated with either lecithin (20%) or with nothing ("slurry") or were exposed to 2% collagen, to 1% polyethylene glycol (PEG), or to 1% carboxymethyl-cellulose (CMC). Solvent was removed using either heat (36° C.), vacuum at room temperature or lyophilization (freeze drying under vacuum). Preparations were also made with a 2% OTC solution in ethanol (EtOH) removed under vacuum with or without Table 2 describes the finished product in terms of the following properties:

Weights of carrier matrix (by weighing) and OTC (by analysis). Averages±SD were obtained from 5 samples.

"Physical state" describes the appearance and mechanical properties of the Matrix. These varied from pliable to crusty to hard (hrd.) to shriveled (shr.). "Dark." indicates the the OTC had darkened.

"OTC dist. (macro.)" describes the macroscopic OTC distribution of OTC in the Matrix after dissecting it and observing it in cross section under an ultra-violet light. It was rated as grossly homogeneous (homog.) if OTC was observed in all portions of the Matrix and as heterogeneous (heterog.) when it was not.

"Assoc (micro.)" describes the microscopic distribution of OTC in relation to the fibers. It was determined using a fluorescent microscope, observing dry samples and their behavior upon re-wetting. The following modes of association were observed:

Very loose association (VLA): OTC Microcrystals have few discernible points of contact with fibers under microscopic examination. In these cases OTC dust is released when the preparation is torn apart or shaken.

Loose association (LA): Microscopic examination shows that the OTC Microcrystals have few points of contact with fibers. Under microscopic examination the Microcrystals invariably become dislodged when water is added to isolated fibers.

Close association (CA): Microscopic examinations shows that the OTC Microcrystals are in intimate contact with fibers. No space can not be discerned between Microcrystals and the fibers to which they are bound. Under microscopic examination the Microcrystals could be dislodged from isolated fibers after water was added and the fibers were agitated.

Continuous close association (CCA): Observations were the same as CA except that the complete surface area of the fiber is covered with OTC.

Very close association (VCL): Intimate contact as in CA but OTC Microcrystals could not be dislodged from isolated fibers by soaking and agitation.

Solid continuous block (SCB): Microcrystals of OTC coat the fibers and fill much of the space between the fibers. Table 2 also describes the rate of release of Drug Microparticles from the hydrated Matrix observed under the microscope (Examples 13–20).

EXAMPLE 3

Lecithin-Oxytetracycline-Collagen Matrix and Lecithin-Oxytetracycline-Cellulose Matrix An aqueous suspension of 20% (w/v) oxytetracycline (OTC), 20% (w/v) lecithin microcrystals was prepared by the process described in Example 1 except that the source of lecithin was Ovothin$^R$ 120 (Lucas Meyer, Decatur, Ill.) and the final pH was 5.0. Gelfoam® and cellulose fiber gauze (from "Non-Stick Pad", Johnson & Johnson, New Brunswick, N.J.) were cut, measured. They were then impregnated with the above suspension by manipulation (squeezing and allowing to reform). The excess liquid was removed by blotting and the samples were dried by heat treatment or lyophilization as indicated. With the Gelfoam® samples, the relationships between initial volume, hydrated, dried and rehydrated volume were similar to those described in Example 2. For the cellulose fiber gauze samples, the original dimensions were 3×10×15 mm (0.45 cm$^3$). With addition of lecithin-coated OTC microcrystals they increased thickness by approx. 50% (0.675 cm$^3$) and held this volume when suspended by a surgical forceps. Upon lyophilization they retained this volume. The volume was unchanged upon rehydration.

FIG. 1 presents schematic representations of fragments of the preparations cut from the samples based on observations under the microscope at 10× and 40×. Material was deposited on and between the fibers of the carrier materials within the matrix.

The characteristics of the finished products are given in the first grouping in Table 2. Lyophilization gave pliable products with homogeneous distribution of oxytetracycline (OTC) throughout the dressing, with close association between the microcrystals and the fibers. Under the microscope, individual OTC Microcrystals with 0.5 to 2$\mu$dimensions could be easily discerned from their strong yellow-green fluorescence. Panel A of FIG. 2 is a reproduction of a transmission photomicrograph of a coated collagen fibril dissected from the preparation and viewed at 800 power. Panel B of FIG. 2 shows exactly the same field illuminated in the ultra-violet which causes OTC to give off yellow-green fluorescence depicted as white in this reproduction.

In this Example the OTC/carrier weight ratios were 3.14±0.35 gm/gm for Gelfoam® and 2.29±0.44 gm/gm for the cellulose gauze. The products are suitable for both insertion into surgical sites and as external wound dressings. The Gelfoam® material can be loaded with OTC to approx. 4.0 gm/gm and still retain this property.

Removal of water by warm drying in air caused the Gelfoam®-based preparation to become shriveled and hard, and caused the gauze-based preparation to darken.

EXAMPLE 4

OTC-Collagen Matrix and OTC-Cellulose Matrix

This is a comparative example, showing the effect of omitting lecithin (or other adjuvant). The procedure of Example 3 was repeated except that lecithin was omitted and sonication (Sonifier® Cell Disrupter, Mod. W 185D, Heat System and Ultrasonics, Plainview, N.Y.) was used for particle size reduction. In attempt to minimize crystal reaggregation, the Gelfoam® and gauze samples were rapidly impregnated. Volume relationships were similar to those described in Examples 2 and 3, for Gelfoam® and gauze, respectively. As shown in the second grouping of Table 2, the distribution of OTC within the two types of matrix was heterogeneous. The microcrystals were loosely or very loosely associated with the collagen matrix and cellulose matrix, respectively. A lower degree of OTC incorporation was obtained for the Gelfoam®-based preparation. The samples were pliable, and are suitable for external wound dressings. However, the samples are not resistant to continuous vibration.

EXAMPLE 5

Collagen-OTC-Collagen Matrix and Collagen-OTC-Cellulose Matrix

Oxytetracycline (OTC) was sonicated in buffer in the presence of 2% (w/v) collagen (Insoluble Type I Bovine Achilles Tendon, C-9879, Lot 21F-8000, Sigma Chemical Co., St. Louis, Mo.). The sonication was performed for 60 min. at 30–40° C. Gelfoam® samples were impregnated and lyophilized. Volume relationships were similar to those described in Example 2 except that the sample did not swell to its original volume when it was rehydrated. It remained at its low volume (<0.2 cm$^3$, or <40% original volume) for at least 15 hrs.

The lyophilized sample was a crusty and hard. The matrix could be shaped by compression and could be easily torn apart or trimmed without loss of OTC. Under microscopic examination, the Gelfoam®-based preparation had clumps of 2–5 $\mu$m microcrystals (strong yellow-green fluorescence) entrapped between the original and added collagen. This material is suitable for implantation in bone.

When cellulose gauze was used as a carrier material, a crusty and hard material was also obtained. Volume relationships were as described in Example 3. Microscopic examination revealed clumps of 2–5 $\mu$m OTC Microcrystals (yellow-green fluorescence) embedded in flakes of collagen loosely adhering to the cellulose fibers. This emphasizes the need for the adjuvant to have affinity for both the drug microparticle and the carrier material.

EXAMPLE 6

PEG-OTC-Collagen Matrix and PEG-OTC-Cellulose Matrix

OTC was sonicated at 20% (w/v) in the presence of 1% (w/v) polyethylene glycol (PEG) (m.w. 3,350, P-3640, Lot 127F-0214, Sigma Chemical Co., St. Louis, Mo.). For Gelfoam®, inclusion of this non-ionic surfactant did not improve the adhesion of the OTC-Microparticles, but produced a less pliable product in the dry state (Table 2). For the gauze preparation, inclusion of PEG did not improve the adhesion of the OTC-Microparticles and did not change the pliability of the product. Volume relationships were as described in Examples 2 and 3, respectively.

EXAMPLE 7

CMC-OTC-Collagen Matrix and CMC-OTC-Cellulose-Cellulose Matrix

The procedure of Example 4 was repeated, except that the sonication was done in the presence of 1% (w/v) carboxymethylcellulose (CMC) (sodium salt, C-8758, Lot 67F-0527, Sigma Chemical Co., St. Louis, Mo.). Treatment of Gelfoam® and gauze materials with this macromolecule increased the hardness of the material and did not improve the adhesion of the OTC-Microparticles (Table 2). Volume relationships were as described in Examples 2 and 3, respectively.

EXAMPLE 8

Lecithin-OTC-Collagen Matrix and Lecithin-OTC-Cellulose Matrix from an Ethanol Medium An ethanolic solution of 2% (w/v) OTC and 2% (w/v) lecithin was made and the Gelfoam® and gauze samples were wetted with this solution and dried at room temperature under vacuum. This cycle was repeated for a total of 5 times. The procedure resulted in homogeneous OTC distribution in the finished collagen matrix and cellulose matrix. Under the microscope, 1–4 $\mu$m microcrystals were observed. Some were in clumps, but all were in close or very close association with the cellulose fibers or collagen fibers, respectively. The products are pliable and are suitable for both insertion into surgical sites and for use as external wound dressings. The degrees of OTC loading were lower than in Examples 3 and 4. The volumes of the samples did not change with immersion in ethanol solution, dehydration or rehydration.

EXAMPLE 9

OTC-Collagen Matrix and OTC-Cellulose Matrix from an Ethanol Medium

Example 8 was repeated, except that lecithin was not included. This also resulted in pliable finished products with low degrees of loading, and with looser association between the drug and fibers. The volumes of the samples did not change with immersion in ethanol solution, evaporation or hydration.

EXAMPLES 10–12

Drug Release, Macroscopic Observations

In these examples, materials from previous examples were tested for the rate of release of oxytetracycline. The samples were introduced into vials containing 2.0 ml of 300 mM mannitol, 2 mM phosphate buffer, pH 7.0. The samples became completely hydrated within 1–15 minutes. Gelfoam®-based samples expanded from their dry volume (<0.2 cm$^3$) to their pre-impregnated volumes of approx. 0.50 cm$^3$. The exception was collagen-OTC-Gelfoam® which did not expand. All the gauze-based samples retained the volumes of their treated states (1.5 times original volume).

After several minutes of hydration the samples were compressed once (to approx. ⅒th of their original volume) against the wall of the container to squeeze out any oxytetracycline which was not associated with the carrier material. The samples were then removed and introduced into a new vials with new buffer and the process was repeated at the end of 3-hour intervals for up to 15 hours. The cumulative amount of oxytetracycline released was calculated. The data are shown in FIG. 3.

EXAMPLE 10

OTC release from Lecithin-OTC-Collagen Matrix and PEG-OTC-Collagen Matrix

Figure 1A:
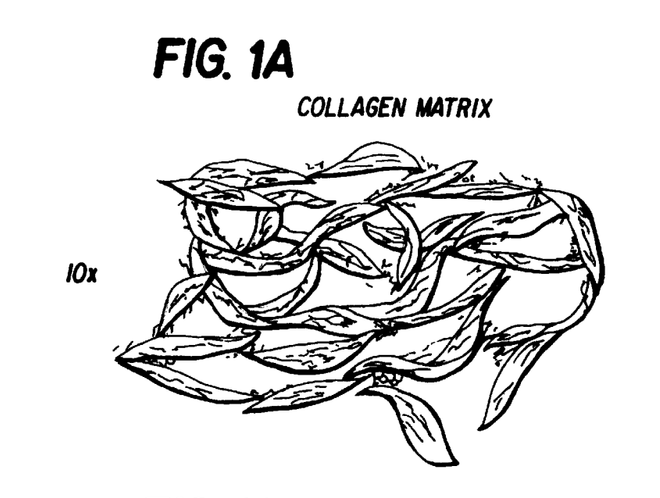
Figure 1B:
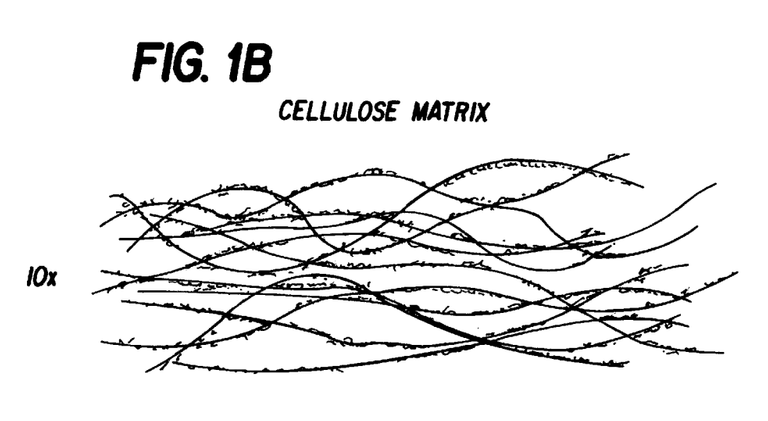
Figure 1C:
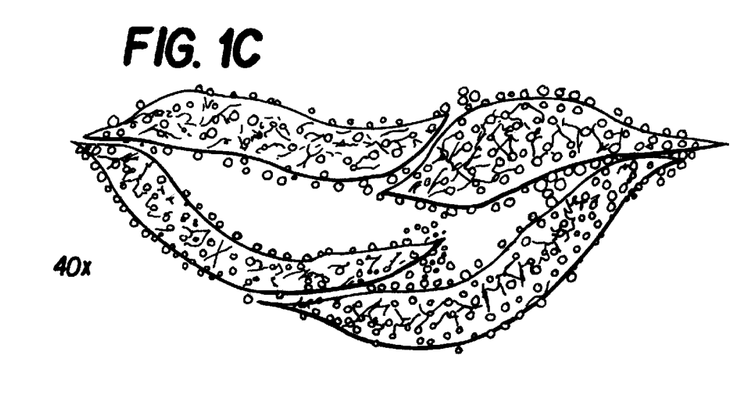
Figure 1D:
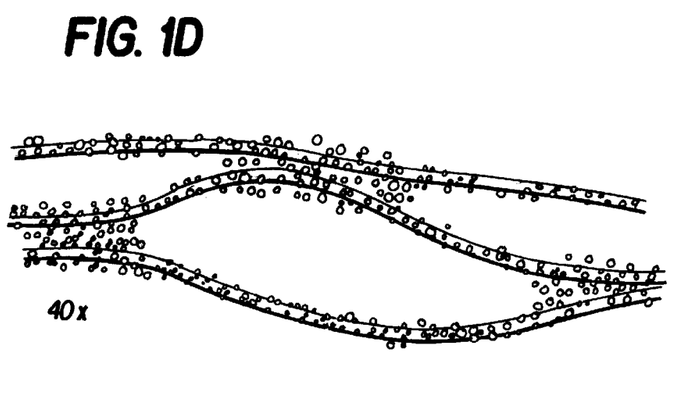
Figure 2A:
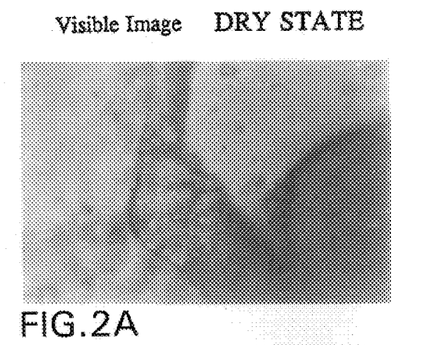
FIG. 2 presents reproductions of 800× photomicrographs of a collagen fibril dissected from a Lecithin-Oxytetracycline-Collagen Matrix. Panel A is from a transmission photomicrograph. Panel B depicts the yellow-green fluorescence (represented as white) arising from the associated oxytetracycline microcrystals in the identical specimen when illuminated by ultra-violet light. Panels C and D are from photo- and fluorescent micrographs (respectively) of another specimen after hydration with aqueous buffer.
Figure 2B:
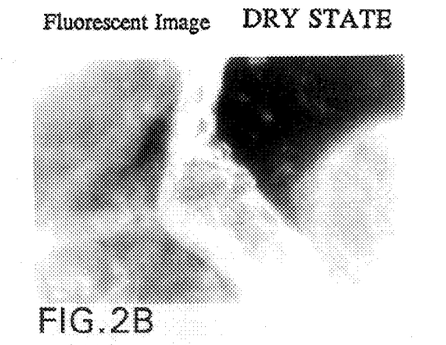
Figure 2C:
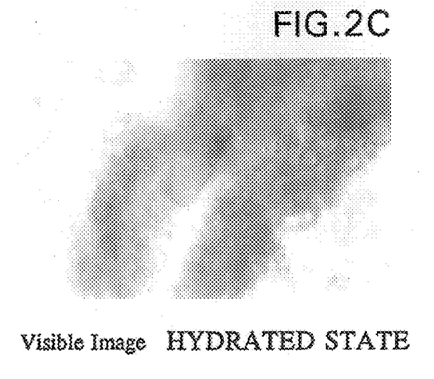
Figure 2D:
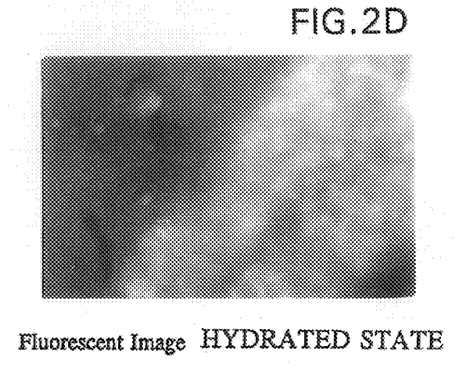
Figure 3:
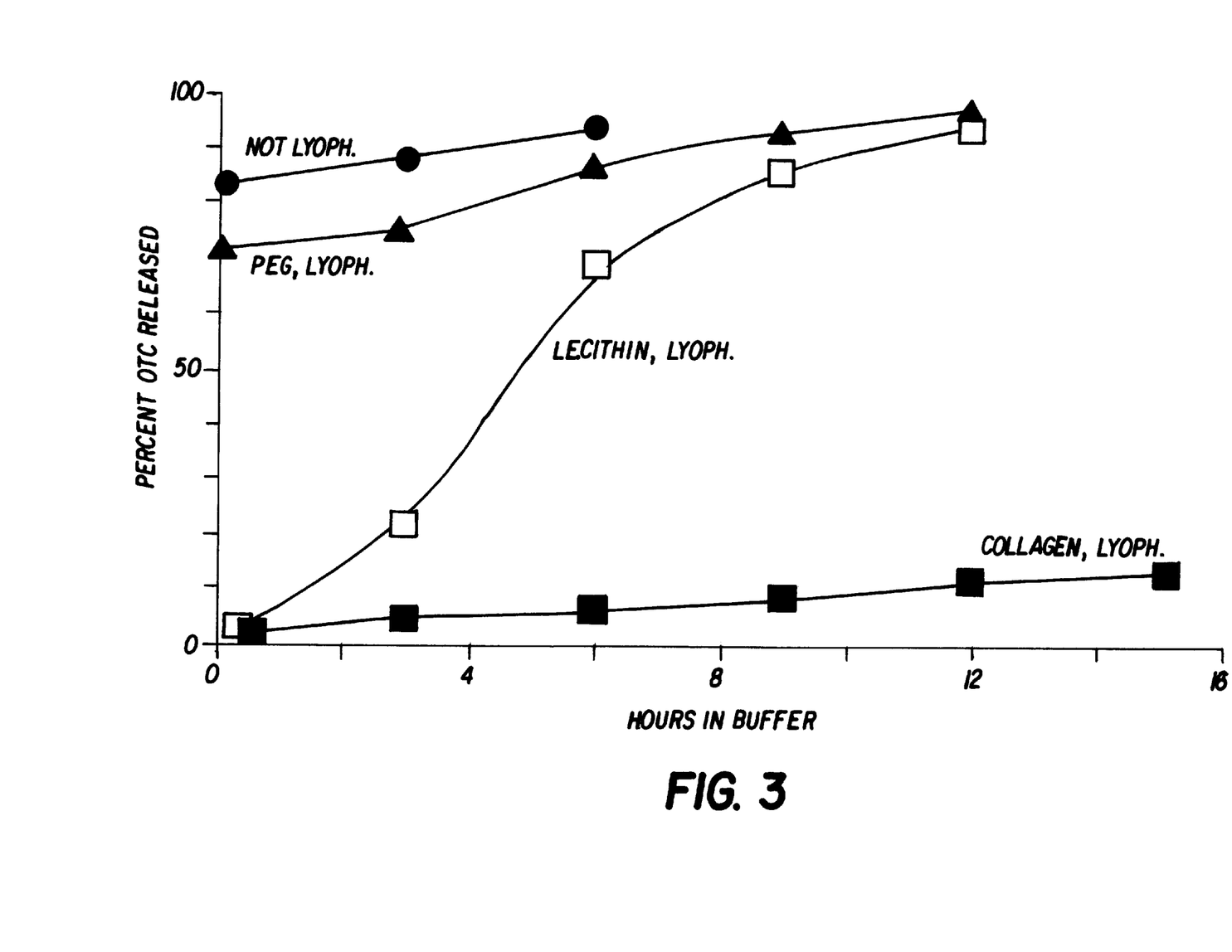
FIG. 3 shows the time course of oxytetracycline release from four forms of oxytetracycline-impregnated Collagen Matrix. Details of the experiment are given in Examples 10–12.

The top trace of FIG. 3 is a control experiment which shows that when Gelfoam® is simply impregnated with an aqueous suspension of lecithin-coated OTC microcrystals, but not dried or lyophilized, the OTC is released quickly. The center trace in FIG. 3 shows that Lecithin-OTC-Gelfoam prepared by lyophilization in Example 3 releases its OTC slowly. In this test, 6 hours are required to release 70% of the OTC. Similar results were obtained with samples which had been dried at 36° C. The comparison shows that the lyophilization or drying has caused the lecithin-coated OTC microcrystals to be bound to the collagen fibers of the collagen matrix.

FIG. 3 shows that PEG-OTC-collagen matrix (lyophilized) releases OTC very rapidly, indicating that PEG does not provide a firm attachment of the OTC to the collagen matrix.

The above experiments also showed that the release of OTC was by release of OTC microparticles (Mechanism B). When the carrier material was squeezed the solution became cloudy, indicating that colloidal material was released. Also, the amounts of OTC released into certain 2.0 ml aliquots (approx. 10 mg) exceeded the solubility of OTC (1.1 mg/ml at pH 7.0).

EXAMPLE 11

OTC release from Collagen-OTC-Collagen Matrix

FIG. 3 shows that Collagen-OTC-Collagen Matrix prepared by lyophilization gives very slow release of OTC. Only 15% of the incorporated OTC was released in 15 hours. This shows that the addition of collagen increases OTC retention. Microscopic examination of this preparation showed that microcrystals were physically entrapped in a matrix of solid collagen material. In this experiment, the release was consistent with Mechanism A (release of OTC monomers). No cloudiness was observed in the solution, and the free concentration of OTC in the aliquots was ≦0.6 mg/ml which is well below its solubility limit (1.1 mg/ml).

EXAMPLE 12

Lecithin-OTC-Collagen Matrix and OTC-Collagen Matrix from Ethanol Solution

The release rates were also determined for the Gelfoam®-based samples of Examples 8 and 9, prepared by impregnation with ethanolic solutions of 2% OTC with or without 2% lecithin, respectively. Under the conditions of FIG. 3, 70% release of OTC from the lecithin/OTC loaded preparation required 6 hrs. For the preparation without lecithin, 70% release required approx. 14 hr. This difference may relate to the larger size of the OTC crystals obtained in the absence of lecithin.

EXAMPLES 13–20

Drug Release, Microscopic Observations

EXAMPLE 13

OTC release from Lecithin-OTC-Collagen Matrix, Microscopic Observations

The fragment of the Lecithin-OTC-Collagen Matrix sample from Example 3 was removed and was mounted between a slide and coverslip, buffered isotonic mannitol was added, and the process of hydration and OTC release was visualized using the fluorescence microscope at 800-fold magnification. By switching from ultraviolet excitation to transmitted light, OTC microcrystals could be discerned from lecithin and the collagen carrier material. Within 2–3 minutes of addition of the medium, changes in light transmission could be observed, with the collagen fibers becoming more diffuse. Within 5 minutes, some OTC microcrystals were being released from the edge of the preparation, where they exhibited Brownian motion. Lecithin and OTC microcrystals which were intimately associated with the collagen fibrils could be observed to bud and swell. Panels C and D of FIG. 2 represent transmission and fluorescent photomicrographs of a coated collagen fibril within the preparation. The OTC microcrystals are more widely separated.

Close to the edge of the hydrated preparation immobilized individual OTC microcrystals could be discerned. Within the center of the 0.1–1.0 mm dimensioned material, OTC microcrystals were at high concentration, were immobilized and individual microcrystals could not be discerned. However, OTC microcrystals could be made to flow out in "rivers" when the sample was squeezed by manipulating the coverslip. The released OTC microcrystals were of fairly uniform size estimated to be in the 0.3–0.7 $\mu$m range.

This behavior was graded as slow release. (See Table 2, last column.)

EXAMPLE 14

OTC Release From PEG-OTC-Collagen Matrix, Microscopic Observations

The experiment of Example 13 was repeated using the PEG-OTC-Collagen Matrix preparation of Example 6. The sample changed shape immediately after the addition of aqueous medium. The movement and streaming removed OTC microcrystals within 20 sec. Manipulation of the coverslip showed that the microcrystals could be readily squeezed out, indicating a lack of affinity for the collagen matrix. The released OTC microcrystals ranged in size between an estimated 0.1 and 5.0 $\mu$m.

This behavior was graded as rapid release (see Table 2, last column).

EXAMPLE 15

OTC Release from CMC-OTC-Collagen Matrix, Microscopic Observations

The experiment of Example 13 was repeated using CMC-OTC-Collagen Matrix from Example 7. Rapid release was observed, with observations comparable to those of Example 14.

EXAMPLE 16

OTC Release from OTC-Collagen Matrix, Microscopic Observations

The experiment of Example 13 was repeated using the OTC-Collagen Matrix preparation of Example 4, lacking adjuvant. As with PEG-OTC-Collagen Matrix (Example 14), microcrystals were rapidly dissociated, indicating a lack of affinity for the collagen matrix. The microcrystals were predominantly 2–5 $\mu$m.

EXAMPLE 17

OTC Release from Collagen-OTC-Collagen Matrix, Microscopic Observations

The experiment of Example 13 was repeated using the Collagen-OTC-Collagen Matrix of Example 5. The matrix did not change shape or optical properties even 30 minutes after the addition of aqueous medium. The yellow fluorescence of the OTC remained within the mass of the collagen matrix, and only occasional 0.5–5.0 $\mu$m microcrystals could be discerned on the edge. Ninety minutes after the addition of the aqueous medium, manipulation of the coverslip did not dislodge OTC microcrystals. This behavior was graded as very slow release (see Table 2, last column). From this, and from the release experiment of Example 11, we concluded that microcrystalline OTC is firmly lodged in the collagen matrix.

EXAMPLE 18

OTC Release from Lecithin-OTC-Collagen Matrix (Ethanol Preparation), Microscopic Observations The experiment of Example 13 was repeated using Lecithin-OTC-Collagen Matrix of Example 8 prepared by evaporation of ethanol. Slow release was observed, comparable to that seen in with lyophilized Lecithin-OTC-Collagen Matrix in Example 13.

EXAMPLE 19

OTC Release from OTC-Collagen Matrix (Ethanol Preparation), Microscopic Observations The experiment of Example 13 was repeated using OTC-Collagen Matrix of Example 9 prepared by evaporation of ethanol. One-half of the OTC was rapidly released. The remainder was released slowly as with Lecithin-OTC-Collagen Matrix.

EXAMPLE 20

OTC Release from Cellulose Gauze Matrices, Microscopic Observations

The experiments of Examples 13–19 were repeated using the cellulose gauze preparations and the results are tabulated in the final column of Table 2.

The above examples and teachings show how one skilled in the art can select (1) the carrier material, (2) the drug to be incorporated, (3) the adjuvant, and (4) the method of preparation to get optimal mechanical properties and drug release characteristics for use as a therapeutic wound dressing or implant.

To summarize the preferred embodiment of our invention, water-insoluble drugs are reduced to 20 nm–30 $\mu$m size in aqueous suspension, mixed with defined adjuvant materials and soaked into existing surgical materials consisting of fibers, fabrics or solid foams and water is removed by lyophilization. The finished product constitutes a surgical material capable of delivering large quantities of drug to the surrounding tissue at defined rates. The choice of drug concentration and adjuvant materials and method of incorporation can be used to control the rate of drug release from the surgical material. The modes of incorporation involve physico-chemical affinity of the adjuvant for both the microcrystalline drug and the surgical material. Alternatively the adjuvant can serve as an aid to entrapment of the drug microcrystal between the fibers of the surgical material. The drug-containing material is implantable if the existing surgical material from which it is formed is implantable. The drug-containing material can also be used as an external dressing. Water-soluble drugs can be incorporated in the surgical materials. Their rates of release can be controlled by encapsulation within phospholipid membranes, by adjuvants which render them insoluble, or by a combination of these principles.

The implant of the present invention may be used in surgical or dental procedures wherein it is desired to simultaneously control bleeding and deliver a drug to adjacent tissue. In particular, contemplated uses include closing the skin or laceration for pain/infection control; decreasing inflammation and preventing keloid formation when closing skin; after thoracotomy for pain control to enhance ventilation thereby preventing pneumonia; after herniorraphy when laid upon the ilioinguinal nerve as it is exposed for pain control; after surgery in a contaminated area to deliver antibiotics; after all types of surgery for infection control; after orthopedic surgery to provide bone growth stimulating factors to the site; after orthopedic surgery to provide pain relief, which facilitates joint movement which facilitates recovery; after wounding on the battlefield to provide pain relief, hemostasis, infection control during transport when applied topically or to exposed parenteral areas of the body.

The present invention provides a pliable, implantable material, suitable for use in surgery and dental practice, which releases a drug or biological agent to the surrounding tissue over a chosen period to achieve a therapeutic effect. Our invention can also be used as a removable wound dressing. Our invention can also provide a semi-rigid material which is suitable for implantation in bone, and which is capable of releasing a drug or biological agent over long periods of time. In particular, contemplated uses include implanting the device during surgery to provide pain relief, implantation during orthopedic surgery to provide inflammation relief thereby quickening the rehabilitation process, implantation post dental extraction in the tooth socket for pain control; when impregnated with materials to hasten bone healing it will be implanted along sites of fracture to improve healing of bone; when impregnated with antibiotics it will be implanted during surgery to provide sustained release of antibiotics to the local area; when impregnated with materials to improve clotting it will be implanted during surgery or post dental extraction to facilitate hemostasis; when used topically it will be applied to provide pain relief if impregnated with anesthetics/analgesics; when impregnated with antibiotics it will be applied to prevent or treat infection.

Further aspects of our invention include the ability to control the rate and mode of release of the drug by choice of concentration and type of adjuvant used, as well as the ability to incorporate the drug at high payload (up to 4 gm Drug/gm Carrier Material). Thus, drugs can be delivered at high concentrations to the adjoining tissue for long durations to prevent the growth of bacteria, to facilitate wound healing and to even give systemic drug delivery, when needed. Additionally, the use of adjuvants to adjust the release rates for water-insoluble and water-soluble drugs is a significant aspect of our invention.

In conclusion, the present invention provides a means of giving continuous treatment of a wound or surgical site with a drug. When used with a resorbable carrier material, our invention provides an implantable sustained delivery device for the drug, achieving local therapeutic benefit while providing hemostasis and a controlled environment for tissue regeneration. It provides a large reservoir of drug at the site where it is needed, but in the form of drug microparticle with controlled association with the carrier matrix material.

With the foregoing and other objects, advantages and features of the invention that will become hereinafter apparent, the nature of the invention may be more clearly understood by reference to the following detailed description of the invention, the appended claims and to the several views illustrated in the attached drawings.

What is claimed is:

1. A drug delivering surgical device for internal or external use comprising:

a carrier comprising a pharmaceutically acceptable porous, fibrous matrix for releasably securing coated drug microparticles therein, said fibers having diameters of between about 0.1 micrometers to about 100 micrometers;

wherein said coated drug microparticles between about 20 nanometers to about 20 micrometers in size, releasably bound to said fibrous matrix by attachment or entrapment therein;

said fibers and said drug microparticles are each coated with a coating agent selected from the group consisting of non-crosslinked collagen and gelatin, carboxymethylcellulose, hydroxyethyl cellulose, hydroxypropyl cellulose, hydroxypropyl methylcellulose, polyethylene glycol, povidone, benzalkonium chloride, benzethonium chloride, or long-chain alkylamines.

2. The drug delivering surgical device of claim 1, wherein said drug microparticles are selected from the group consisting of antiseptics, antibiotics, antiinflammatories, local anesthetics, tissue growth promoters, tissue destruction inhibitors, and combinations thereof.

3. The drug delivering surgical device of claim 1, further comprising a preservative.

4. The drug delivering surgical device of claim 3, wherein said preservative is selected from the group consisting of benzethonium chloride, propylparaben, butylparaben, chlorobutanol, benzyl alcohol, phenol, sodium benzoate, and EDTA.

5. The drug delivering surgical device of claim 1, wherein said coated drug microparticles are less than about 10 microns in size.

6. The drug delivering surgical device of claim 1, wherein said carrier retains up to about 4 grams of drug per gram of carrier.

7. The drug delivering surgical device of claim 1, wherein said fibrous matrix is selected from the group consisting of collagen, cross-linked collagen, cross-linked gelatin, cellulose, cellulose, fiberous cellulose acetate, ethyl cellulose, methyl cellulose, fiberous ethyl hydroxyethyl ether cellulose, pyrrolidone, acrylates, polybutyrates, polyvalerates, polyglycolic acid, polyglactin and poly-D,L-lactate.

8. The drug delivering surgical device of claim 7, wherein said fibrous matrix is an absorbable gelatin sponge.

9. The drug delivery device of claim 1, wherein said device is a surgical implant and wherein said porous fibrous matrix consists essentially of chemically-crosslinked collagen fibers; wherein said microparticles are coated with collagen or gelatin which are not chemically crosslinked.

10. The drug delivery device of claim 1, wherein said device is a surgical implant or surgical dressing and said porous fibrous matrix is in the form of a fabric of woven or piled fibers.

* * * * *